United States Patent [19]
Reusch

[11] Patent Number: 5,928,632
[45] Date of Patent: Jul. 27, 1999

[54] SURFACTANT FREE RINSE-OFF SKIN CONDITIONING FORMULATION

[75] Inventor: Rick Reusch, Covington, Ky.

[73] Assignee: The Andrew Jergens Company, Cincinnati, Ohio

[21] Appl. No.: 08/933,985

[22] Filed: Sep. 19, 1997

[51] Int. Cl.⁶ .............. A61K 31/74; A61K 7/06; A61K 7/00
[52] U.S. Cl. .......... 424/78.03; 424/70.1; 424/70.16; 424/401; 514/939; 514/940
[58] Field of Search .............. 424/70.1, 78.03, 424/70.16, 401; 514/939, 940

[56] References Cited

U.S. PATENT DOCUMENTS 5,004,598  4/1991  Lochhead et al. .......... 424/59
5,221,534  6/1993  DesLauriers et al. .......... 424/78.03
5,578,299  11/1996  Starch .......... 424/78.03

*Primary Examiner*—Shelley A. Dodson
*Assistant Examiner*—Marina Lamm
*Attorney, Agent, or Firm*—Oblon, Spivak, McClelland, Maier & Neustadt, P.C.

[57] ABSTRACT

A surfactant free skin conditioning composition comprising a primary emollient of a gelled mineral oil, and emulsion stabilizer including at least one of a high molecular weight homopolymer of polyacrylic acid or a copolymer having a major proportion of a monoolefinically unsaturated carboxylic monomer or its anhydride, of 3 to 6 carbon atoms, and a minor proportion of a long chain acrylate or methacrylate ester monomer, gives superior deposition of skin conditioning emollients when applied to human skin, and rinsed off.

10 Claims, No Drawings

SURFACTANT FREE RINSE-OFF SKIN CONDITIONING FORMULATION

BACKGROUND OF THE INVENTION

1. Field of the Invention

This invention pertains to a skin-conditioning composition which is designed to be applied and rinsed off. More specifically, the inventive composition is intended for use in an environment in which it is applied to human skin, and subsequently rinsed away, leaving a skin-conditioning deposit on the skin's surface which is aesthetically acceptable. The composition is surfactant free.

2. Background of the Invention

Various skin-conditioning compositions exist which are intended to be introduced to bath water, and act as a softener or otherwise condition the skin while bathing. Typical skin conditioning agents include mineral oil or synthetic oils, and in bathing compositions, are of relatively low viscosity, for dispersion in the water. Additionally, polymers are known agents for combining with mineral oils in skin softening compositions, per se.

Other cosmetic compositions particularly designed for skin conditioning include those discussed in U.S. Pat. No. 5,152,991, which is directed to cosmetic compositions containing selectively hydrogenated styrene/butylene copolymers. These copolymers are specifically designed to prevent removal of the composition in which they are formulated, from the skin, or at least to prevent easy washing off of the cosmetic formula.

U.S. Pat. No. 5,143,723 is directed to colored lipstick compositions, or "make-up", such as lipstick, nail coloring and the like. The compositions addressed are intended to exhibit particular brilliance of color, by incorporating a solvated dye into the resins, including styrene block polymers or butylene/ethylene copolymers.

An additional cosmetic composition which employs particulate polymers, rather than a polymer matrix, is addressed in European Patent Application 497,144, that requires particulate styrene/ethylene/propylene copolymer components, as well as conventional emollients and agents such as colorants, UV blockers and the like.

A different type of cosmetic composition is addressed in U.S. Pat. No. 5,221,534, DesLauriers et al., the entirety of which is incorporated herein by reference. This reference is directed to compositions employing mineral oil with blends of di-block and tri-block copolymers based on synthetic thermoplastic resins. In general, the compositions contain 80–99% by weight of an oil, and 1–20% by weight of copolymer which includes at least one of either a di-block or tri-block polymer which consist of a hard segment, such as a styrenic segment, and a soft segment, such as butadiene. Thus, tri-block copolymers of styrene/butadiene/styrene and styrene/isoprene/styrene are employed, as well as di-block copolymers such as a styrene/ethylene/propylene, or styrene/ethylene butylene are employed to gel the oil, imparting a substantially different viscosity. The gel is designed as a carrier for various agents for topical administration. This gelled mineral oil is commercially available under the mark Geahlene, from Penreco, Division of Pennzoil products. Certain of the preparations described herein were made with Geahlene AJ.

An alternate formulation is disclosed in U.S. Pat. No. 5,578,299, Starch, and related U.S. patent application Ser. No. 08/861,108. These applications describe compositions that achieve controlled deposition of skin-conditioning agents, or emollients, by careful control over the amount and type of surfactant employed. As recognized in these patent documents, the deposition of too little of the emollient on the skin, after rinsing, as a residue does not provide a significant conditioning effect. In the alternative, too high a percentage of deposition makes rinsing difficult, and leaves the skin with an oily, greasy feeling. As disclosed in U.S. Pat. No. 5,578,299, incorporated herein by reference, a desirable percentage of the formulation left as a residue on the skin after rinsing is about 3–25%, of the formulation, by weight. Preferred amounts include 6–15%, by weight. U.S. Pat. No. 5,578,299 and pending U.S. patent application Ser. No. 08/861,108, achieve control over the amount of emollient deposited in particular, Geahlene, by controlling the amount of surfactant incorporated, and the type of surfactant. The need to use and control surfactant composition carefully, however, limits the range of optional ingredients that can be incorporated in the formulation, and raises the possibility of skin irritation.

While U.S. Pat. No. 5,221,534 provides a method for depositing topical agents without the use of a surfactant, and may itself provide certain skin conditioning properties, since the product is in the form of a gel, deposition directly on the skin leaves an undesirable feeling.

U.S. Pat. No. 5,004,598, Lochhead et al., discloses a quick-breaking water-in-oil emulsion containing mineral oil and a Pemulen polymer that breaks on contact with the skin. The active agent is a modified polymer which is a copolymer having a major proportion of a monoolefinically unsaturated carboxylic acid monomer or its anhydride of 3 to 6 carbon atoms and a minor proportion of a long chain acrylate or methacrylate ester monomer. The disclosure of U.S. Pat. No. 5,004,598 is incorporated herein by reference.

U.S. Pat. Nos. 5,043,155, Puchalaski et al., and 4,837,019, Georgalas et al., describe emollients which contribute to emulsion stability, and are generally comprised of glyceryl polymethacrylate, propylene glycol and a poly(vinyl-methyl ether) maleic anhydride (PVM/MA) copolymer. These compositions are available as Lubragel oil, manufactured by Guardian Chemical, while the emulsion stabilizer comprised of the glyceryl polymethacrylate and propylene glycol, without the PVM/MA is available under the name Lubragel CG. The disclosure of U.S. Pat. No. 5,043,155 is incorporated herein by reference.

Other emollients used in the art for skin conditioning include octyl isononanoate, which is typically used in conjunction with mineral oil, to provide a certain amount of "slip", or reduce the greasy feel provided by mineral oil. U.S. Pat. Nos. 5,527,488 and 4,722,835 exemplify this use.

Carbopol polymers available from B. F. Goodrich have also been explored as possible emulsifiers. These agents are acrylic acid or homopolymers, generally of the formula $(C_3H_4O_2)_n$, which are subsequently cross-linked, to give a molecular weight of about 1 million–4 million. U.S. Pat. No. 5,004,598 examines the use of such polymers as emulsifiers in emulsions, column 9, line 50 - column 10, line 2, and finds they lead to unstable emulsions.

None of the compositions available to those of ordinary skill in the art simultaneously provide adequate skin conditioning effect, with a controlled deposition of 3–25% by weight of the composition after rinsing, an acceptable feel, and in the absence of surfactants. The provision of such a skin conditioning formulation continues to be an object of those of skill in the art.

SUMMARY OF THE INVENTION

The invention comprises a surfactant free skin conditioning formulation which combines the gelled mineral oil of U.S. Pat. No. 5,221,534 with an emulsion stabilizer that can be the modified copolymer of U.S. Pat. No. 5,004,598, commercially available as Pemulen, or a carbomer such as one of the carbopol polymer series, a lightly cross-linked homopolymer of acrylic acid of molecular weight 1 million–4 million, or a combination of the two, as the active agents in a surfactant-free skin conditioning formulation which, when rinsed off, leaves between 3–25% by weight of the formulation on the skin. As gelled mineral oil is one of the components, the formulation advantageously employs octyl isononanoate as an emollient to lower the greasy feeling contributed by the gelled mineral oil, available as Geahlene from Pennzoil.

Improved feel, and emulsion stability, is preferably contributed by polyglyceryl methacrylate and propylene glycol, alone or together with PVM/MA copolymer, available as Lubragel and Lubragel Oil from Amerchol.

The high concentration of acrylic acid moieties contributed by the Pemulen, carbomer or both, may require neutralization, using a gentle amine or other acceptable base, such as dilute sodium hydroxide.

DETAILED DESCRIPTION OF THE INVENTION

The inventive formulation is intended to be applied to the skin, followed by rinsing. After rinsing, a significant (3–25%) proportion of the emollient composition must remain on the skin to provide skin conditioning. Applicants have discovered that neither the modified polymer of U.S. Pat. No. 5,004,598, nor the gelled mineral oil of U.S. Pat. No. 5,221,534, provides effective amounts of deposition after rinsing, coupled with an aesthetically acceptable feel. Similarly, high molecular weight homopolymers of acrylic acid, carbomers such as those available under the mark Carbopol, fail to provide an effective skin conditioning composition. It is Applicants' discovery that the combination of the gelled mineral oil as a primary emollient, together with at least one of the modified copolymer of U.S. Pat. No. 5,004,598 or carbomer in appropriate concentration provide the desired deposition, without the use of surfactants. The greasy feeling contributed by the gelled oil can be made aesthetically acceptable by the addition of octyl isononanoate, while the addition of Lubragel or Lubragel oil improves emulsion stability.

Gelled Mineral Oil

The gelled mineral oil of U.S. Pat. No. 5,221,534 is the primary emollient of the inventive formulation. An exemplary commercially available gel is Geahlene 500, which is a mixture of mineral oil, polystyrene-poly(ethylene/butylene)-polystyrene tri-block copolymer and poly (ethylene/propylene)-polystyrene di-block copolymer, of which approximately 7% by weight is copolymer. Typically, the ratio of di-block to tri-block copolymer, by weight, is in the range of 2:1–1:3. Typically, the gelled mineral oil (considering the mineral oil and copolymer together) is present in the composition in an amount of 15–20%, by weight of the entire composition.

Emulsion Stabilizer

The composition importantly includes an emulsion stabilizer, in addition to the gelled mineral oil. The stabilizer is an essential emulsifier that forms a stable emulsion without the use of surfactants. This emulsion stabilizer can be either a modified copolymer, such as that disclosed in U.S. Pat. No. 5,004,598, or a lightly cross-linked acrylic acid homopolymer such as the Carbopol polymer series available from B. F. Goodrich, wherein the molecular weight is about 1 million–4 million. The modified polymer is a copolymer having a major proportion of a monoolefinically unsaturated carboxylic acid monomer, or its anhydride, of 3 to 6 carbon atoms, and a minor proportion of a long chain acrylate or methacrylate ester monomer. Suitable monoolefinically unsaturated carboxylic acid monomers include acrylic acid and maleic anhydride. Suitable esters include decyl acrylate, lauryl acrylate, stearyl acrylate, behenyl acrylate, and the like, as well as corresponding methacrylates.

In the alternative, the emulsion stabilizer may be a carbomer, a high molecular weight acrylic acid homopolymer, such as the Carbopol polymers available from B. F. Goodrich. Carbopol ETD2050 is an exemplary product.

Preferably, the emulsion stabilizer is a combination of the modified copolymer and carbomer. The modified copolymer provides an emulsion form which breaks quickly upon application to the skin, releasing the oil phase immediately and permitting rapid rinsing, while the carbomer provides enhanced viscosity and physical stability. The emulsion stabilizer is present in amounts of 0.2–2.0%, by weight of the total composition.

The primary emollient, the gelled mineral oil, and the emulsion stabilizer, constitute the essential elements of the formulation. These may be combined, directly with water, to provide an effective skin conditioning agent. The feel, appearance and aesthetics of the formulation can be improved, however.

Additional Components

Octyl isononanoate is widely available, and is advantageously included as a tertiary emollient that is effective in its own right, and reduces the greasy feeling of the gelled mineral oil employed as the primary emollient. The amount employed will vary with the amount of primary emollient, and is generally present in about 25%, by weight, of the primary emollient. A preferred range is from 4–10%, by weight of the entire composition.

The composition described is extremely effective in depositing a highly desirable amount, 3–25%, by weight, of the formulation, on the skin after rinsing. The "feel" of the deposited material can be improved by the incorporation of a Lubragel, or a Lubragel oil product. This is a combination of polyglyceryl methacrylate and polypropylene glycol, together, or in combination with a polyvinyl methacrylate/methacrylate copolymer. This agent is present in an amount of 1–5%, by weight, again dependent on the concentration of primary and secondary emollients in the formulation.

The pH of the product is preferably very slightly acidic, to match the natural pH of skin. A pH of approximately 5.5–6.5 is desired. The secondary emollient/emulsion stabilizer employed in the invention presents a significant concentration of acrylic acid functional moieties. It may be necessary to neutralize these moieties to achieve the desired pH. Neutralization is preferably achieved by using a weak base, such as triethanolanime, available from Dow Chemical. In the alternative, other bases customarily used in skin conditioning formulations, such as dilute sodium hydroxide, may be employed. The concentration of any neutralizing agent is tied quite closely to the concentration of the secondary emollient/emulsion stabilizer, and ranges from 0.2–2%, by weight.

Optional Ingredients

Skin conditioning agents typically employ optional ingredients that achieve improvement in aesthetics, or marketability. Thus, colorants (typically a whitening pigment such as a titanium oxide particle), a preservative and stabilizer, as well as a fragrance may be included. A wide variety of preservatives are available to those of ordinary skill in the art. Germaben II, available from ISP Sutton, is easily incorporated into cold process manufacturing, available in a liquid form. This agent is a combination of diazolidinyl urea, methylparaben, propylparaben and propylene glycol. As the composition is prepared by simply cold mixing of the oil and water phases, followed by blending of the two, this preservative provides adequate protection against bacteria, mold and yeast contamination, without complicating the manufacturing process.

Additional optional agents include topically active ingredients, such as sun screen agents, topical antibiotics, anti-acne agents, and the like. Numerous agents that can be incorporated in the oil phase are identified in U.S. Pat. No. 5,221,534, and may be incorporated herein as well. Other agents, suitable for incorporation in the water phase, may also be incorporated.

The balance of the formulation is water, preferably a deionized water. The water serves as a vehicle for carrying the oil phase.

EXAMPLES

Applicants have prepared inventive formulas (Formulas A–C), embodying the claimed invention, which employ both the combination of the carbomer and modified copolymer, as well as one or the other, as the secondary emollient/emulsion stabilizer. These have been compared with the formulations of the prior art discussed above, and examples from U.S. Pat. No. 5,004,598, which also describes a surfactantless emulsion. These emulsions were tested for percentage deposition following rinsing. The compositions were prepared by conventional blending and evaluated with respect to the amount of residue left after rinsing. The test involves the application of the composition to a hydrated plastic film. The film is then rinsed under running water, dried and weighed to determine how much residue is deposited. This test simulates the application conditions of the composition onto human skin after rinsing, or in the shower. Actual human testing demonstrates that the standardized experiment correlates with the experience of those who used formulas of different compositions under the same experimental conditions. Beyond the residue test, the compositions were inspected to determine the emulsion stability. The results are reflected in Table 1 hereto. As can be seen, the inventive compositions provided a stable emulsion, with deposition of between 3–25% by weight of the formulation. In contrast, the comparative formulas, and formulas of other surfactantless emulsions, did not provide adequate deposition.

This invention has been disclosed generically, and by specific embodiment and example. The exemplaries provided are representative only, and alternatives will occur to those of ordinary skill in the art without the exercise of inventive faculty. Alternatives remain within the scope of the invention, unless excluded by the recitations of the claims set forth below.

TABLE 1

|  | Inventive Formula A | Inventive Formula B | Inventive Formula C | Comparative Formula A | Comparative Formula B | Comparative Formula C | Pat. 5,004,596 Example 64 | Pat. 5,004,856 Example 66 |
| --- | --- | --- | --- | --- | --- | --- | --- | --- |
| WATER PHASE |  |  |  |  |  |  |  |  |
| Water | 66.20 | 88.40 | 88.40 | 66.20 | 79.15 | 75.00 | 84.80 | 82.70 |
| Pemululen (1) | 0.15 | 0.30 | — | 0.15 | — | — | 0.40 | 0.20 |
| Carbomer | 0.15 | — | 0.30 | 0.15 | — | — | — | — |
| Propylene Glycol | 0.56 | 0.56 | 0.56 | 0.56 | — | — | 1.00 | — |
| Methylparaben | 0.11 | 0.11 | 0.11 | 0.11 | 0.20 | — | 0.20 | 0.20 |
| Propylparaben | 0.03 | 0.03 | 0.03 | 0.03 | — | — | — | — |
| Diazolidinyl Urea | 0.30 | 0.30 | 0.30 | 0.30 | — | — | — | — |
| Glycerin | — | — | — | — | 5.00 | — | 5.00 | — |
| PEG-8 | — | — | — | — | — | — | — | 0.50 |
| Lubragel CG (2) | 1.00 | — | — | 1.00 | — | — | — | — |
| Lubragel Oil (3) | 1.00 | — | — | 1.00 | — | — | — | — |
| OIL PHASE |  |  |  |  |  |  |  |  |
| Geshlene AJ (4) | 23.70 | 7.40 | 7.40 | — | 10.00 | 25.00 | — | — |
| Mineral Oil | — | — | — | 23.70 | — | — | 5.00 | 13.00 |
| Octyl Isononanoate | 6.30 | 2.60 | 2.60 | 6.30 | — | — | — | — |
| Caprylic Capric Triglycerides | — | — | — | — | — | — | — | 2.00 |
| Cetearyl Alcohol | — | — | — | — | 2.50 | — | 1.00 | — |
| Cetyl Alcohol | — | — | — | — | — | — | — | 0.50 |
| Ceteareth-20 | — | — | — | — | 1.00 | — | — | — |
| Stearic Acid | — | — | — | — | 0.50 | — | — | — |

TABLE 1-continued

|  | Inventive Formula A | Inventive Formula B | Inventive Formula C | Comparative Formula A | Comparative Formula B | Comparative Formula C | Pat. 5,004,596 Example 64 | Pat. 5,004,856 Example 66 |
|---|---|---|---|---|---|---|---|---|
| Ethylene Glycol Monostearate | — | — | — | — | — | — | 1.00 | — |
| Cetyl Acetate & Acetylated Lanolin Alcohol | — | — | — | — | — | — | 0.60 | — |
| Cetyl Esters Wax | — | — | — | — | 0.50 | — | — | — |
| Dimethicone 200 cst. | — | — | — | — | 0.50 | — | 0.50 | — |
| Propylparaben | — | — | — | — | 0.10 | — | 0.10 | 0.20 |
| Triethanolamine 99% | 0.30 | 0.30 | 0.30 | 0.30 | — | — | 0.40 | 0.40 |
| Sodium Hydroxide 50% sol'n | — | — | — | — | 0.25 | — | — | — |
| DMDM Hydantoin | — | — | — | — | 0.30 | — | — | 0.30 |
| Fragrance | 0.20 | — | — | 0.20 | — | — | — | — |
| TOTAL: | 100.00 | 100.00 | 100.00 | 100.00 | 100.00 | 100.00 | 100.00 | 100.00 |
| Initial (24 Hr.) Stability Check | No Separation | No Separation | No Separation | No Separation | No Separation | Separation | No Separation | No Separation |
| Average Film Deposition | 4.01% | 3.00% | 5.71% | 2.05% | 0.24% | N/A | 0.76% | 0.98% |

(1) Acrylates/C10-30 Alkyl Acrylate Crosspolymer
(2) Glyceryl polymethacrylate and Propylene Glycol
(3) Glyceryl polymethacrylate and Propylene Glycol and PVM/MA copolymer
(4) Mineral Oil and Hydrogenated Butylene/Ethylene/Styrene Copolymer and Hydrogenated Ethylene Propylene Styrene Copolymer

What is claimed is:

1. A surfactant free skin conditioning composition, comprising an oil-in-water emulsion, comprising:
   a) a first emollient comprised of gelled mineral oil comprised of mineral oil in a copolymer mixture comprising an ethylene/propylene/styrene copolymer and a butylene/ethylene/styrene copolymer present in an amount of 15–30% by weight of the total composition;
   b) an emulsion stabilizer selected from the group consisting of a modified polymer, a homopolymer of polyacrylic acid, and mixtures thereof, wherein said modified polymer is a copolymer having a major proportion of a monoolefinically unsaturated carboxylic acid monomer or its anhydride of 3 to 6 carbon atoms and a minor portion of a long chain acrylate or methacrylate ester monomer, and said homopolymer is lightly cross-linked having a molecular weight (weight average) of 1 million–4 million, said emulsion stabilizer being present in an amount of 0.1–3.0% by weight of the total composition;
   c) 0–10% of at least one of an emollient comprising an alkyl ester of at least 16 carbon atoms, a fragrance, a colorant and a preservative; and the balance water.

2. The composition of claim 1, wherein said composition further comprises an agent which neutralizes acrylic acid moieties in said emulsion stabilizer, and wherein the pH of said composition is between 5.5–7.0.

3. The composition of claim 1, wherein said composition is in the form of an oil-in-water emulsion, which breaks upon application of said composition to human skin, releasing said first emollient from said emulsion.

4. The composition of claim 1, wherein said emulsion stabilizer comprises a mixture of said modified polymer and said homopolymer.

5. The composition of claim 1, wherein said composition is a creamy white lotion having a viscosity of 3000–5000 cps at room temperature.

6. The composition of claim 1, wherein said emulsion comprises a second emollient selected from the group consisting of silicone oils, alkyl esters of at least 16 carbon atoms, petrolatum, ungelled mineral oil, lanolin and mixtures thereof.

7. The composition of claim 1, wherein said emulsion stabilizer is a mixture of said modified polymer and said homopolymer, said composition further comprises triethanolanime, a preservative suppressing the growth of bacteria, mold and yeast and octyl isononanoate.

8. A method of conditioning skin, comprising applying a skin conditioning effective amount of the composition of claim 1 to said skin, allowing said to emulsion to break and release mineral oil to said skin, and allowing said mineral oil to remain on the skin for a time sufficient to effect skin conditioning.

9. The method of claim 8, wherein excess mineral oil deposited on said skin is rinsed away following the breaking of said emulsion.

10. The method of claim 9, wherein, after rinsing, 3–25% by weight of said composition remains on said skin.

* * * * *